United States Patent [19] | [11] 4,358,438
Bijlenga | [45] Nov. 9, 1982

[54] NOVEL POLYVALENT VIRUS VACCINE AGAINST RABIES AND CANINE DISTEMPER

[75] Inventor: Gosse Bijlenga, La Tour de Salvagny, France

[73] Assignee: Gist-Brocades N.V., Delft, Netherlands

[21] Appl. No.: 253,238

[22] Filed: Apr. 13, 1981

Related U.S. Application Data

[62] Division of Ser. No. 168,332, Jul. 14, 1980.

[30] Foreign Application Priority Data

Jul. 17, 1979 [GB] United Kingdom ................. 7924916

[51] Int. Cl.³ .................. A61K 39/175; A61K 39/205
[52] U.S. Cl. ...................................... 424/89; 435/235; 435/239
[58] Field of Search ................... 424/89; 435/235–239

[56] References Cited

U.S. PATENT DOCUMENTS

| | | | |
|---|---|---|---|
| 2,908,614 | 10/1959 | Muggleton et al. | 435/235 |
| 3,155,589 | 11/1964 | Slater | 424/89 |
| 3,228,840 | 1/1966 | MacPherson et al. | 435/235 |
| 3,418,210 | 12/1968 | Sanders | 435/235 |
| 3,632,741 | 1/1972 | Wittmann et al. | 424/89 |

FOREIGN PATENT DOCUMENTS

| | | | |
|---|---|---|---|
| 1270918 | 4/1972 | United Kingdom | 424/89 |
| 2053679A | 2/1981 | United Kingdom | 424/89 |

OTHER PUBLICATIONS

V.B. 46 #1894 (1976); 45 #3131 (1975); 44 #2163 #250 (1974); 42 #2099 (1972);41 #3920 (1971); 35 #2150 (1965); 24 #3438 (1959); 36 #2189 (1966); 27 #479 (1957); 21 #2891 (1951); 43 #5504 (1973) Bijlenga et al.

*Primary Examiner*—Shep K. Rose
*Attorney, Agent, or Firm*—Hammond & Littell, Weissenberger and Muserlian

[57] ABSTRACT

A polyvalent virus vaccine for immunization of warm-blooded animals comprising a mixture of a rabies virus, preferably rabies strain No. 675 deposited in the Czechoslovak National Collection of Type Cultures of the Institute of Hygiene and Epidemiology in Prague under No. CNCTC No. A 04/77, and a canine distemper virus, said mixture being substantially free of material emanating from more than one type of tissue cell used to propagate the viruses and a process for its preparation by infecting a suitable single cell system with a rabies virus strain, propagating the rabies virus, infecting the cell system with at least one canine distemper virus, propagating the viruses and separating the polyvalent vaccine from the propagation product.

7 Claims, No Drawings

NOVEL POLYVALENT VIRUS VACCINE AGAINST RABIES AND CANINE DISTEMPER

This is a division of Ser. No. 168,332 filed July 14, 1980.

STATE OF THE ART

From Can. J. Comp. Med. Vet. Sci., Vol. 28 (1965), p. 38–41, it is known to simultaneously grow rabies virus and canine distemper virus in the same chick embryos but, it is clearly indicated that both viruses are inoculated on different tissues of the embryonated eggs, and thus do not multiply in the same cells. The viruses used were Flury rabies virus (RV) of chick embryo passage between 59 and 61, and canine distemper virus (CD) of chick embryo passage between 55 and 59, while Salmonella-pullorum-free 5 to 6 days old embryonated eggs were selected. The article indicates that bivalent vaccines for rabies and canine distemper could be produced, of which the potencies and virus titres were comparable to those of rabies vaccine and canine distemper vaccine produced separately. These obtained bivalent vaccines have the known general disadvantages of vaccine preparation due to the extraneous tissue material which causes generally known undesired side effects.

British Pat. No. 1,270,918 describes the preparation of multivalent vaccines in a single cell culture by simultaneous cultivation of different viruses causing respiratory diseases, especially viruses selected from the group consisting of (a) respiratory syncytial virus (b) parainfluenza viruses (c) influenza viruses strains A and B (d) infectious bronchitis-"like" virus and (e) mycoplasma pneumoniae. However in the description of the invention on page 1, lines 80–87, it is clearly stated that it was originally believed by people skilled in the art that infection of a cell with one virus type might preclude simultaneous infection of the same cell with a different virus although later on, this theory was tested and proved not to be generally true. Nevertheless, multiple infection of cells has only been shown to be feasible with certain viruses and is not generally applicable.

In British Pat. No. 1,270,918 only specific combinations of viruses, rather similar in type, seemed to be capable of being used for the simultaneous infection of cells and subsequent harvesting of multivalent vaccines. The application of the same process on viruses of really different characteristics, and which also differ from the types of viruses mentioned in British Pat. No. 1,270,918, i.e. rabies and canine distemper, was certainly not described in, or suggested by the disclosure of British Pat. No. 1,270,918.

In particular, because of the difficulties associated with the simultaneous culture of two or more different viruses, all the presently marketed polyvalent vaccines are still prepared by mixing vaccines obtained individually by growing each virus vaccine in separate cell cultures.

Moreover, it will be appreciated that it is known from e.g. Avian Dis. Vol. 7 (1963) p. 106–122; Am. J. Vet. Res. Vol. 17 (1956) p. 294–298 and Avian Dis. Vol. 11 (1967), p. 399–406 and Virology Vol. 33, (1967) p. 598–608, that mixtures of several live vaccines prepared separately and then mixed may lose the original activity of the separate components due to mutual inhibition. The problem of mutual inhibition may occur not only when separate vaccines are mixed, and the preparation of the combined vaccines of the invention during which no substantial interference of the viruses within the same cell system occurs, to yield a combined vaccine product having acceptable titres for both viruses, is surprising.

OBJECTS OF THE INVENTION

It is an object of the invention to provide a novel polyvalent vaccine for the immunization of warm-blooded animals and to provide a novel process for its preparation.

It is another object of the invention to provide a novel method of immunizing warm-blooded animals.

These and other objects and advantages of the invention will become obvious from the following detailed description.

THE INVENTION

The novel polyvalent vaccine of the invention is comprised of at least one living rabies virus and at least one living canine distemper virus substantially free of tissue material derived from more than one type of cell used to propagate the viruses.

The virus strains are propagated in a single cell system by infecting the same cells with two or more different types of viruses. There are considerable advantages in the production of polyvalent virus vaccines by culture of more than one type of virus in the same cell system, for example: 1. Lower production expenses due to lower labor costs and the lower cost of culture media, glasswork, lyophilization, diluents, and packing material resulting in a lower market price of the polyvalent vaccine, and 2. Application of the vaccine to dogs, minks, ferrets and the like by a single inoculation instead of two or more inoculations. In addition, the use of a single cell system for culture of the viruses avoids the disadvantages associated with the use of e.g. chick embryos such as the presence of extraneous animal material in the final product, which causes known undesired side-effects.

As a result of research and experimentation, a process was surprisingly found for the preparation of polyvalent virus vaccines comprising at least one rabies virus and at least one canine distemper virus by propagation of these strains in a single cell system. The process of the invention for the preparation of a polyvalent vaccine comprises at least one living rabies virus and at least one living canine distemper virus by propagating the viruses in a single cell system and recovering the polyvalent vaccine from the propagation product. The process is preferably carried out by first infecting a suitable single cell system with at least one rabies virus strain, propagating the rabies virus, then infecting the cell system with at least one canine distemper virus, propagating the viruses and preparing the polyvalent vaccine from the propagation product.

The invention further provides a polyvalent vaccine comprising a rabies virus and a canine distemper virus substantially free from material emanating from more than one type of tissue cell used to propagate the viruses. The vaccines preferably contain $10^{7.5}$ to $10^{9.2}$ p.f.u./ml of rabies virus and, preferably, $10^{4.5}$ to $10^{7}$ p.f.u./ml of canine distemper virus.

Any canine distemper virus and any rabies virus which can be propagated adequately in vitro and which can be safely used as a living vaccine provoking an adequate protection may be used in the combined rabies-canine distemper vaccine of the invention such as the Wisconsin (FxNO) or Onderstepoort strains (canine distemper) and the strains (rabies), and strains derived therefrom. The preferred rabies virus is the strain No. 675 deposited with the Czechoslovak National Collection of Type Cultures of the Institute of Hygiene and Epidemiology in Prague under No. CNCTC A 04/77, disclosed e.g. in German patent application No. 2803240, and the preferred canine distemper virus is the avianized vaccine strain (Onderstepoort, J. Vet. Res. Vol. 27 No. 1, (1956) p. 19–53).

The time between infections with the two viruses depends on the multiplicity of infection (m.o.i.) of both types of viruses and the host cells employed. It was found that in vitro infection with the rabies virus is not followed by the production of interferon which permits consecutive interferon-susceptible viral infections. Non-simultaneous infection appeared to be possible only in case the multiplication of the primary infection of the cells does not inhibit or interfere with the subsequent infection by another virus type.

Infection of a single cell system with two or more viruses of susceptible cells also depends on the problem of viral adherence to the total of cell surface available. In the case of rabies infection of BHK-21 cells and a subsequent infection with the canine distemper virus, a polycation is used to ensure adherence of the canine distemper virus to the BHK-21 cells.

It will be appreciated that eventually a third virus or additional viruses could be propagated in the single cell system used with such a procedure mainly depending on the absence of (a) interfering substances and (b) possible inhibition of production of specific viral products necessary for the multiplication.

For the propagation of a bivalent vaccine of rabies and canine distemper in a single cell system, monolayer cultures may be employed, but, any other adequate system such as cell suspension cultures, cell-covered beads in suspension and multiplate cultures can be used for the propagation of the viruses in those cells. Such systems usually increase the virus yield due to the fact that more cells for infection and multiplication are available in a smaller quantity of medium compared with stationary monolayer cultures.

In a preferred process of the invention, the polyvalent vaccines are prepared by growing the virus strains in monolayers of primary or secondary chicken embryo fibroblasts derived from SPF 10 days old chicken embryos or in monolayers derived from other cells of avian origin or mammalian cells, e.g. the BHK-21 (Baby Hamster Kidney cell line—21 passages). Also BHK-21 13S (13 passages in suspension culture) suspended cultures may be used with good results.

In a preferred process of the invention, culture cells, e.g. BHK-21 culture cells, are grown in monolayers for three to four days until confluency, preferably in BHK-21 medium containing 10% tryptose phosphate broth and 10% inactivated newborn calf serum in the presence of antibiotics (e.g. 100 IU of penicillin and 100 micrograms of streptomycin), the confluent monolayer is infected, preferably with the rabies vaccine strain 675, in a multiplicity of infection (m.o.i) preferably between 0.01 and 1 per cell and incubated preferably for 45–60 minutes at 36° C., the virus-containing liquid is then removed, fresh maintenance medium [e.g. a BHK-21 medium and 0.2% bovine serum albumin fraction V with antibiotics (i.e. kanamycin 5% in an amount of 2 ml/1000 ml of medium)] is added and the pH is adjusted to 7.5 to 8.3. After virus multiplication, preferably for 12–36 hours, the maintenance medium is removed and kept sterile for addition after infection of the cells with the canine distemper virus, e.g. the Onderstepoort avianized vaccine strain. The infection of the BHK-21 cells by the second virus is performed in the presence of a suitable polycation which is necessary for the adherence of the virus to them. A suitable polycation, e.g. diethylaminoethyldextran, is generally used in an amount of 50–200, and preferably about 100, micrograms/ml of medium and without this polycation, the canine distemper virus does not adhere to BHK-21 cells. The presence of the polycation may not be necessary for the adherence of the second virus to other cell types. The multiplicity of infection employed for the second virus is preferably 1–0.05, most preferably 0.5–0.05 per cell. After incubation, preferably for 1–2 hours at 36° C., the virus-containing fluid is removed and the original earlier collected maintenance medium is added to the cells.

After one to four days, the cell sheet has been destroyed by the action of both viruses and the medium is harvested with the cell and is frozen. Alternatively, after the distemper virus infection, the cell sheets may be trypsinized and the infected cells put into spinner culture, preferably using $1-5\times10^6$ cells/ml of medium, preferably for 2 to 3 days at 33° C.

After thawing which releases additional amounts of virus from the cells, the cell debris is removed by known methods such as centrifugation or filtration through sterile filters of, e.g. 4 microns pore size, whereafter the cell-free virus-containing liquid is kept at a temperature not exceeding −70° C. Other methods may be used to disrupt the cells after incubation to release additional amounts of virus such as by subjecting the cell suspension to ultrasonic vibration. The expression "known methods" as used in this specification means methods heretofore used or described in the literature.

It will be appreciated that the final polyvalent vaccine prepared by the process of the present invention may contain e.g. suitable stabilizers, preservatives or buffering salts.

The method of the invention for the immunization of warm-blooded animals such as dogs, minks, ferrets and the like comprises inoculation of the warm-blooded animal with a polyvalent vaccine of the invention, preferably subcutaneously or intramuscularly, the latter route being particularly preferred. A suitable and preferred dose of said vaccine is 1–2 ml, depending on the size of the animal, with one booster dose of 1–2 ml after one year. The vaccine may be administered orally or parenterally and the titers of the living viruses are sufficiently high to guarantee an adequate immune response for preventive vaccination against both viral diseases.

In the the following examples there are described several preferred embodiments to illustrate the invention. However, it is to be understood that the invention is not intended to be limited to the specific embodiments.

EXAMPLE 1

BHK-21 cells were grown in monolayers for three to four days until confluency in a BHK-21 medium containing 10% of tryptose phosphate broth and 10% of inactivated newborn calf serum in the presence of 100 IU of penicillin and 100 micrograms of streptomycin and the confluent monolayer was then infected with the rabies virus strain No. 675 in a multiplicity of infection (m.o.i.) between 0.1 and 1 per cell. The monolayer was incubated for 45 minutes at 36° C. and the virus-containing liquid was then removed. Maintenance medium consisting of BHK-21 medium as described above and 0.2% of bovine serum albumin fraction V with 5% of kanamycin in an amount of 2 ml/1000 ml of medium was added to the liquid and the whole medium was adjusted to a pH of 7.8 to 8. After 24 hours of virus multiplication, the maintenance medium was removed and kept sterile for addition after the infection of the BHK-21 cells with the Onderstepoort avianized distemper virus strain. The infection of the cells by the second virus was performed in the presence of 100 micrograms of diethylaminoethyldextran per ml of medium which was necessary for the adherence of the virus to the cells. Without the use of this polycation, canine distemper virus did not adhere to BHK-21 cells. The multiplicity of infection employed for the second virus was 0.1 per cell. After incubation for one hour at 36° C., the virus-containing fluid was removed and the original maintenance medium, which was collected earlier, was added to the cells.

Approximately two or three days later, the cell sheet had been destroyed by the action of both viruses and the medium was harvested with the cells and was frozen. After thawing which released additional amounts of virus from the cells, the cell debris was removed either by centrifugation or by filtration through sterile filters (4 micron pore size). The cell-free virus-containing liquid was frozen and kept at −70° C. and a small sample of the cell-free liquid was removed for titration of the viability of the two viruses.

The rabies virus in the harvest was titrated by the plaque titration technique on BHK-13 S cells in agarose suspension and the titration technique had the advantage that plaques of the rabies virus only appear as the canine distemper virus does not produce plaques in this system. The latter virus is titrated on African green monkey kidney cells (VERO) by the monolayer technique with the cells being covered by agarose after infection.

The titres of the living rabies virus vaccine in several harvests varied between $10^{7.5}$ to $10^{8}$ p.f.u/ml and in the same harvests the canine distemper virus vaccine titred between $10^{4.5}$ to $10^{5}$ p.f.u. per ml. These titres for living viruses for vaccine purposes were sufficiently high to guarantee an adequate immune response for preventive vaccination against both viral diseases.

EXAMPLE 2

BHK-21 13 S cells were grown in monolayers for three to four days until confluency in BHK-21 medium containing 10% of inactivated newborn calf serum in the presence of 100 IU of penicillin and 50 micrograms of streptomycin. The confluent monolayer was then infected with rabies virus strain No. 675 in a multiplicity of infection (m.o.i.) between 0.01 and 1 per cell and was incubated for 45 minutes at 36° C. The virus-containing liquid was then removed and maintenance medium consisting of BHK-21 medium as described above and 0.2% of bovine serum albumin fraction V with antibiotics (i.e. kanamycin in the amount of 50 micrograms/ml of medium was added thereto. The whole medium was adjusted to a pH of 7.8 to 8 and after 24 hours of virus multiplication, the maintenance medium was removed. The cells were then infected with Onderstepoort avianized distemper virus strain in the presence of 100 micrograms of diethylaminoethyldextran per ml of medium for the adherence of the virus to the cells. The m.o.i. employed for the distemper virus was 1 per cell to theoretically infect all cells. After incubation for one hour at 36° C., the virus-containing fluid was removed and the original maintenance medium, which was collected earlier, was added to the cells.

Approximately 6 hours after the distemper virus infection, the cell sheets were trypsinized and the infected cells were put into spinner culture in the amount of $10^{6}$ cells/ml of medium. After two to three days of keeping the spinner culture at 33° C., the medium was harvested with the (dead) cells and was frozen. After thawing which released additional amounts of virus from the cells, the cell debris was removed either by centrifugation at 4° C. or by filtration through sterile filters (4 micron pore size) keeping the harvest cool during this procedure to avoid a drop in titre of the distemper virus. The cell-free virus-containing liquid was frozen and kept at −70° C. and a small sample of the cell-free liquid was removed for titration to determine the viability of the two viruses.

The titration was carried out in vitro as described in Example 1. The average titres of the rabies virus vaccine varied between $10^{8.5}$ to $10^{9.2}$ p.f.u./ml and the same harvests contained an amount of canine distemper virus vaccine between $10^{6}$ and $10^{7}$ p.f.u./ml.

Only living rabies vaccine can be used in this production procedure as the final product containing also distemper virus vaccine loses its potency after inactivation. By proceeding as described above using HEP Flury vaccine instead of the vaccine strain 675, repeatedly similar results have been obtained but with slightly lower titres of the rabies virus ($10^{8.2}$–$10^{9}$ p.f.u./m.).

Various modifications of the vaccines and process and method of the invention may be made without departing from the spirit or scope thereof and it is to be understood that the invention is intended to be limited only as defined in the appended claims.

What I claim:

1. A polyvalent virus vaccine comprising propagating first a living rabies virus and then a living canine distemper virus in a single cell substantially free from material emanating from more than one type of tissue cell used to propagate the viruses in an amount sufficient to combat rabies and canine distemper.

2. A vaccine of claim 1 wherein the rabies virus is selected from the group consisting of the Flury strain and strain No. 675 deposited with the Czechoslovak National Collection of Type Culture of the Institute of Hygiene and Epidemiology in Prague under CNCTD No. A 04/77.

3. A vaccine of claims 1 or 2 wherein the canine distemper virus is selected from the group consisting of Wisconsin (FxNO) strain and Onderstepoort avianized vaccine strain.

4. A vaccine of claim 1 wherein the rabies virus is strain No. 675 and the canine distemper virus is the Onderstepoort avianized vaccine strain.

5. A vaccine of claim 1 wherein the titre of rabies virus is $10^{7.5}$ to $10^{9.2}$ p.f.u./ml.

6. A vaccine of claim 1 wherein the titre of canine distemper virus is $10^{4.5}$ to $10^{7}$ p.f.u./ml.

7. A vaccine of claim 4 wherein the titre of rabies virus is $10^{7.5}$ to $10^{9.2}$ p.f.u./ml and the titre of canine distemper virus is $10^{4.5}$ to $10^{7}$ p.f.u./ml.

* * * * *